(12) United States Patent
Romeas et al.

(10) Patent No.: US 6,223,068 B1
(45) Date of Patent: Apr. 24, 2001

(54) COMPACT RADIOLOGY INSTRUMENT

(75) Inventors: René Romeas, Palaiseau; Eric Maurincomme, Buc, both of (FR)

(73) Assignee: GE Medical Systems, S.A. (FR)

( * ) Notice: Subject to any disclaimer, the term of this patent is extended or adjusted under 35 U.S.C. 154(b) by 0 days.

(21) Appl. No.: 09/184,718

(22) Filed: Nov. 2, 1998

(30) Foreign Application Priority Data

Oct. 31, 1997 (FR) .................................................. 97 13697

(51) Int. Cl.$^7$ ....................................................... A61B 5/05
(52) U.S. Cl. ..................... 600/427; 600/428; 600/429; 600/436; 606/130; 378/901; 378/4; 378/21; 378/41; 378/62; 378/64; 378/68; 378/138; 378/145
(58) Field of Search ............................ 606/130; 600/407, 600/425, 428, 429, 436; 378/901, 4, 21, 41, 62, 64, 68, 145, 138

(56) References Cited

U.S. PATENT DOCUMENTS

| | | | |
|---|---|---|---|
| 3,991,310 | * 11/1976 | Morrison | 378/65 |
| 4,419,763 | 12/1983 | Hawman | 378/149 |
| 5,769,787 | * 6/1998 | Lemelson | 600/407 |
| 5,855,582 | * 1/1999 | Gildenberg | 606/130 |

FOREIGN PATENT DOCUMENTS 2728471  6/1996  (FR) .

* cited by examiner

Primary Examiner—Marvin M. Lateef
Assistant Examiner—Jeoyuh Lin
(74) Attorney, Agent, or Firm—Jay L. Chaskin

(57) ABSTRACT

The radiology instrument contains a source emitting X-radiation, a radiological image receiver, a chassis arranged between the X-ray source and the image receiver in order to accommodate an object to be radiographed, and a positioning and guiding device which can be connected to the chassis and can intercept the X-radiation so as to position and guide probes intended to interact with the object. The positioning and guiding device has first means forming a retractable guide grid having holes whose respective axes converge towards the focal point of the source when the first means intercept the conical radiation, and a retractable positioning grid with holes.

5 Claims, 5 Drawing Sheets

COMPACT RADIOLOGY INSTRUMENT

BACKGROUND OF THE INVENTION

The invention relates to radiology instruments, for example, for neurological or vascular use.

A neurology instrument of this type is generally composed:

- of an X-ray tube and a collimator for forming and delimiting the X-ray beam,
- of an image receiver, generally a radiological image intensifier associated with a video camera,
- of a positioner which carries the assembly consisting of the X-ray tube and the collimator, as well as the radiological image intensifier and the video camera, this positioner being capable of moving in space about at least two orthogonal axes, possibly about three axes, and
- of a table provided with a plate which is intended to support the patient in a recumbent position.

In the case when the positioner is provided with three axes of rotation, the orientation in space of two axes depends on the angle of rotation about a vertical axis. These angles of rotation are orthogonal towards one another and intersect at a point which is referred to as the isocentre of the positioner. This configuration makes it possible to orientate the axis of the X-ray beam in almost all directions in space. The plate of the table can moved along three orthogonal axes so as to position patient correctly with respect to the isocentre of positioner.

The X-ray tube is powered by a high-voltage generator, and the images output by the video camera are processed, displayed and stored in an image processing system.

A radiological instrument of this type may, in particular, be used for performing interventions using a device which is referred to as a stereotaxy frame. This frame makes it possible to immobilize the patient's head using four metal points inserted into the cranium in small holes drilled into the bone by the surgeon.

This chassis is associated with a positioning and guiding device so as to intercept the X-radiation with a view to positioning and guiding probes intended to interact with the patient's head, for example probes intended to be introduced into the patient's cranium. At the present time, radiological instruments of this type require special rooms using two high-power sources of X-radiation, arranged orthogonally with respect to one another at a very large distance from the patient, typically at a distance greater than or equal to 5 meters, so as to obtain quasi-parallel radiation at the patient's head.

Once the patient has been positioned, the surgeon injects a contrast product into the vessels of the head and acquires radiological images of the patient's head. The vessels are visible by virtue of the contrast product. The surgeon then arranges, between the chassis and the image receiver, a perforation guide which, in the case in point, is composed of a thick grid, typically 30 mm thick, perforated with about one hundred holes having parallel axes. The surgeon then acquires an image of the grid superposed with the stereotaxy chassis and the patient's head, then by superposing the image containing the opacified vessels and the image containing the grid on a luminous screen, he determines which holes in the grid do not lie opposite vessels. The surgeon can therefore position the probes facing selected holes and use these guide holes to perforate the patient's cranium.

Further to the fact that an instrument of this type has the major drawback of requiring a special room, because of its very large size, the use of a thick grid to locate the position of the probes almost completely masks the internal anatomical structures of the object to be radiographed, in the case in point the patient's head.

BRIEF SUMMARY OF THE INVENTION

It is therefore desirable to provide a radiological instrument of this type considerably more compact.

It is further desirable to use a probe positioning device which does not completely mask the internal anatomical structures of the object to be radiographed.

In an embodiment of the invention a radiology instrument, comprising a source emitting X-radiation, a radiological image receiver, a chassis arranged between the X-ray source and the image receiver in order to accommodate an object to be radiographed, and a positioning and guiding device which can be connected to the chassis and can intercept the X-radiation so as to position and guide probes intended to interact with the object.

According to an embodiment of the invention, the radiation which is emitted by the source and intercepted by the positioning and guiding device is conical. Moreover, the positioning and guiding device has first means forming a retractable guide grid having holes whose respective axes converge towards the focal point of the source when the first means intercept the conical radiation. The positioning and guiding device also has second means forming a retractable positioning grid with holes. The positions of the positioning holes relative to the chassis and therefore relative to the object to be radiographed when the second means are positioned so as to intercept the conical radiation correspond to those of the guide holes relative to the chassis when the first means are positioned so as to intercept the conical radiation, this positional correspondence accounting for the convergent nature of the axes of the guide holes.

DETAILED DESCRIPTION OF THE INVENTION

Figure 1:
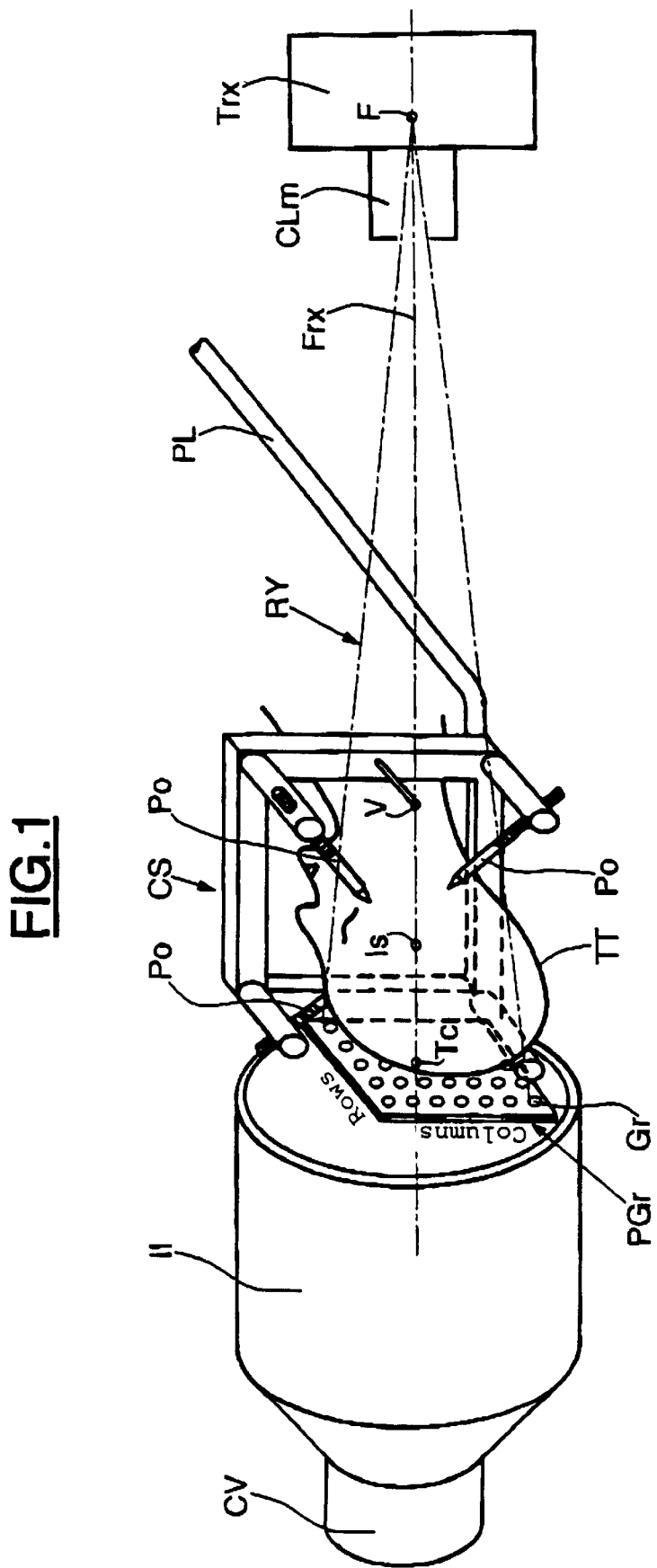
FIG. 1 schematically and partially illustrates a radiology instrument equipped with a chassis and a thin positioning grid.

In FIG. 1, the reference PL denotes a rigid plate which is transparent to X-rays and can be moved in three orthogonal directions in space, in order to position a patient with a view to a radiological examination.

The radiology instrument furthermore includes a positioner (not shown here for the sake of simplicity), generally a C-shaped arm which, on one side, supports an X-ray source referenced Trx and its associated collimator CLm and, on the other side, an image receiver composed of an image intensifier 11 and a video camera CV. The positioner can be rotated about three orthogonal directions in space so as to position the radiological equipment according to the examination to be performed.

The radiological instrument furthermore includes a high-voltage generator supplying the X-ray tube Trx, as well as a system for acquiring and digitally processing the images, and equipment for monitoring and displaying images. All these conventional elements have not been shown in FIG. 1 for the sake of simplicity.

A stereotaxy chassis CS is mounted at the end of the plate PL. The patient's head is immobilized in conventional fashion in the chassis using four points Po inserted into the cranium. The middle of the patient's head is then positioned at the isocentre Is of the positioner (which is the point of convergence of the three axes of rotation of the positioner) close to the axis Frx of the conical radiation RY emitted by the tube Trx from the focal point F.

A thin support PGr, supporting a very thin perforated grid Gr, is inserted between the patient's head and the image intensifier 11. This support PGr is fixed rigidly on the stereotaxy chassis. The thickness of the support/grid assembly, typically of the order of 1 to 2/10 mm, makes it possible to use conical radiation.

The grid Gr may consist of a printed circuit similar to an electronic printed circuit. The support of this metal grid must, of course, be transparent to X-rays, and the metal grid itself may consist of a copper layer having a thickness of the order of 100 to 200 microns. This thickness of copper allows the grid to be seen clearly on the radiological images without completely masking the anatomical structures. Furthermore, the use of image processing for subtracting different images can make the grid or the anatomical structures more clearly visible.

An alignment element, such as a metal ball V, is mounted on the chassis on the opposite side from the positioning grid Gr. This element V makes it possible to align the X-ray imaging system properly.

In order to obtain this alignment, the operator moves the positioner until he obtains perfect alignment of the object focal point F of the conical radiation RY with the ball V and the central hole in the grid Tc.

Figure 2:
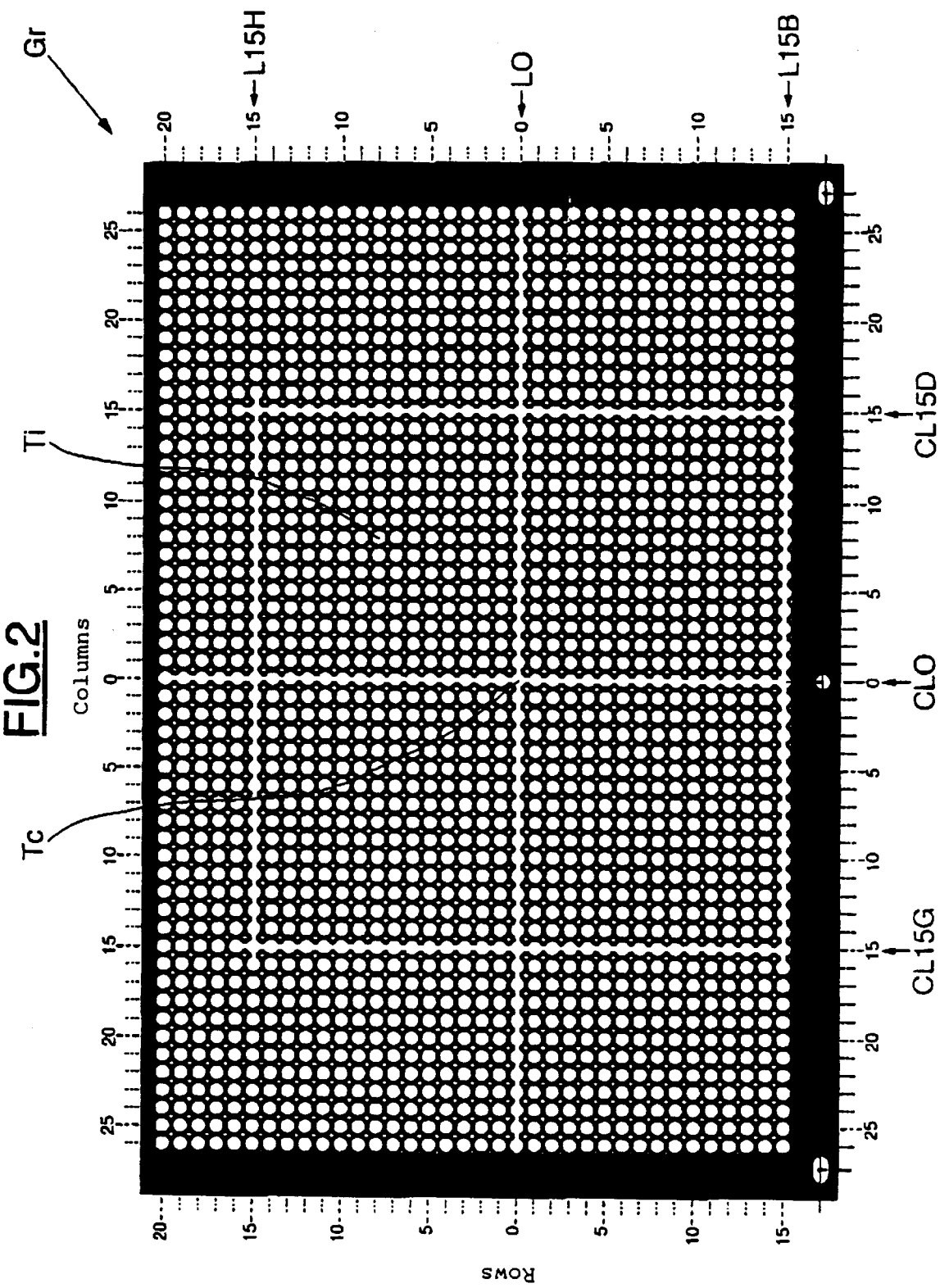
FIG. 2 illustrates the structure of a thin positioning grid in more detail, and FIGS. 3 to 5, respectively, represent schematic front, plan and left views of a chassis equipped with a perforated guide element for forming the probe guide grid.

As can be seen more particularly in FIG. 2, in particular in order to make it easier to recognize the central hole Tc, the holes in the central column CL0 and the holes in the central row L0 communicate. Furthermore, again with a view to facilitating location on the radiological image which is obtained, a frame has been formed in the grid Gr by making some of the holes in rows L15H and L15B and columns CL15G and CL15D communicate.

Once the alignment procedure has been carried out, the operator acquires two images. The first is of the patient's head (in which the vessels have not been opacified with the contrast product) on which the grid has been superposed. The second image is of the patient's "unopacified" head without the positioning grid. These two images will subsequently make it possible to subtract either the patient's head or the grid digitally from the opacified images.

The operator then injects the contrast product into the vessels and acquires a set of opacified images of the patient's head.

All the images are stored in the memory of the image processing system.

The surgeon can then locate the best positions for inserting the probes into the patient's cranium. To this end, he may use subtracted or unsubstracted images with electronic superposition of the grid directly on the display screen. Better accuracy can thus be obtained because of the clearer visibility of the vessels in the subtracted images, in particular owing to the use of a very thin positioning grid.

In order to guide the tool for perforating the cranium, the thin plate PGr supporting the positioning grid Gr may be replaced by a thick perforated grid. This being the case, it is necessary to establish perfect correspondence between the position of the holes in the guide grid and the position of the holes in the positioning grid. However, although the thickness of the positioning grid makes it possible to make positioning holes with parallel axes, even when there is a conical X-ray beam, the thickness of the guide grid, typically a few centimeters, does not allow it to be made with parallel holes. In consequence, the axes of the guide holes in the thick guide grid must all converge towards the object focal point F. Furthermore, because the axes of the guide holes are not parallel, the position of the holes in the positioning grid Gr must be calculated so that the conical projection of the guide holes into the plane of the thin positioning grid corresponds to the actual position of the holes in this positioning grid.

More precisely, referring to FIG. 2, the abscissa x of the positioning hole Ti (the abscissa being counted positively along the line L0 towards the right in FIG. 2) is determined by the formula:

$$D \cdot \tan(nV \times \theta)$$

while the ordinate of this hole Ti (counted positively along the column CL0 from the central hole upwards in FIG. 2) is given by the formula $$\frac{D \cdot \tan(nH \times \theta)}{\cos(nV \times \theta)}$$

In these two formulae, D denotes the distance to the positioning grid Gr from the object focal point, nV denotes the rank of the hole, counted horizontally from the central column, while nH denotes the rank of the hole counted vertically from the central row. Finally, θ denotes the angle between two holes in the grid Gr seen from the focus F of the tube Trx. θ is equal to 0.22° in the embodiment which is described.

It would, of course, also be possible to replace the thick guide grid by a set of two grids which are spaced apart, in particular with a view to reducing weight.

Figure 3:
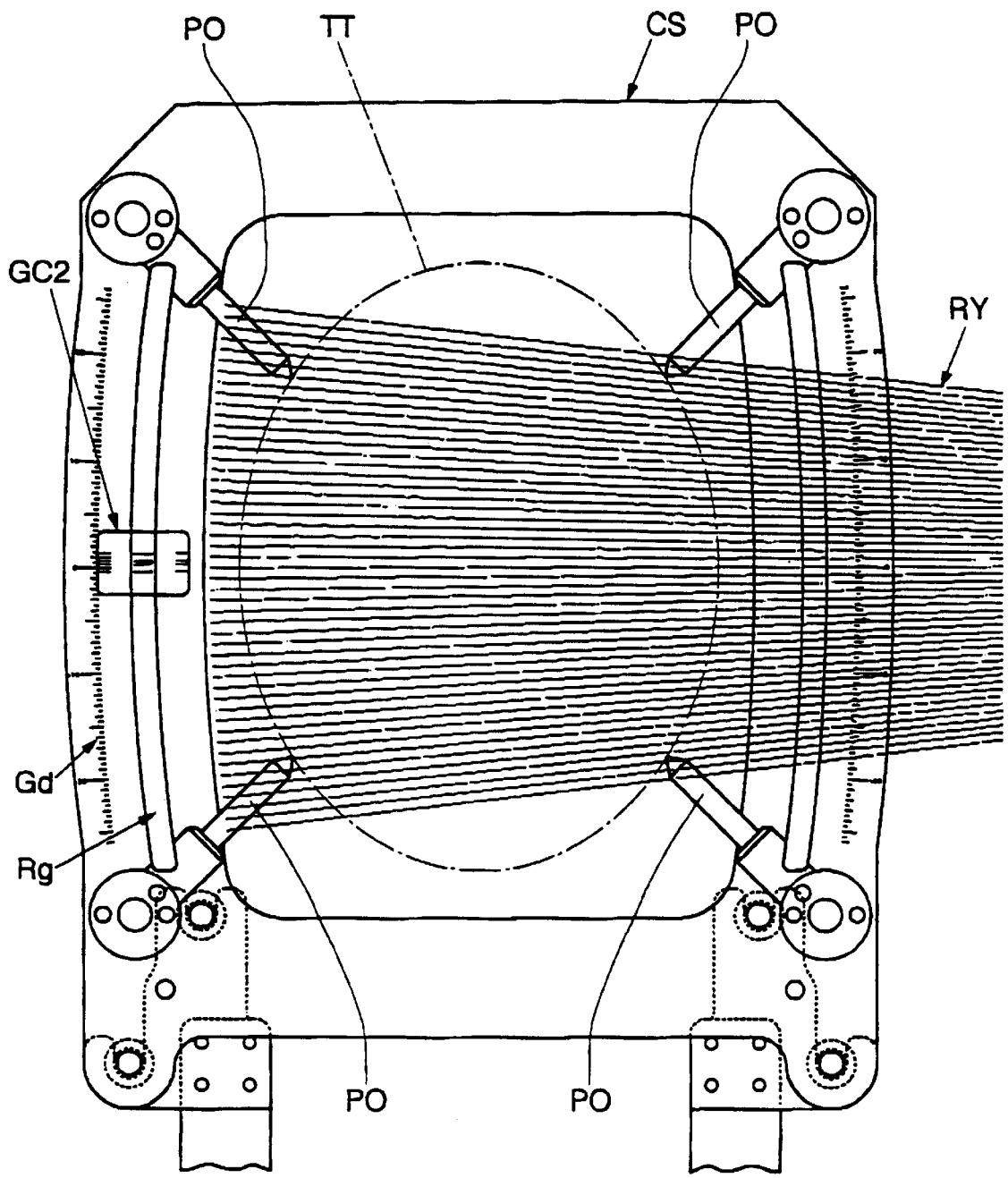
Figure 4:
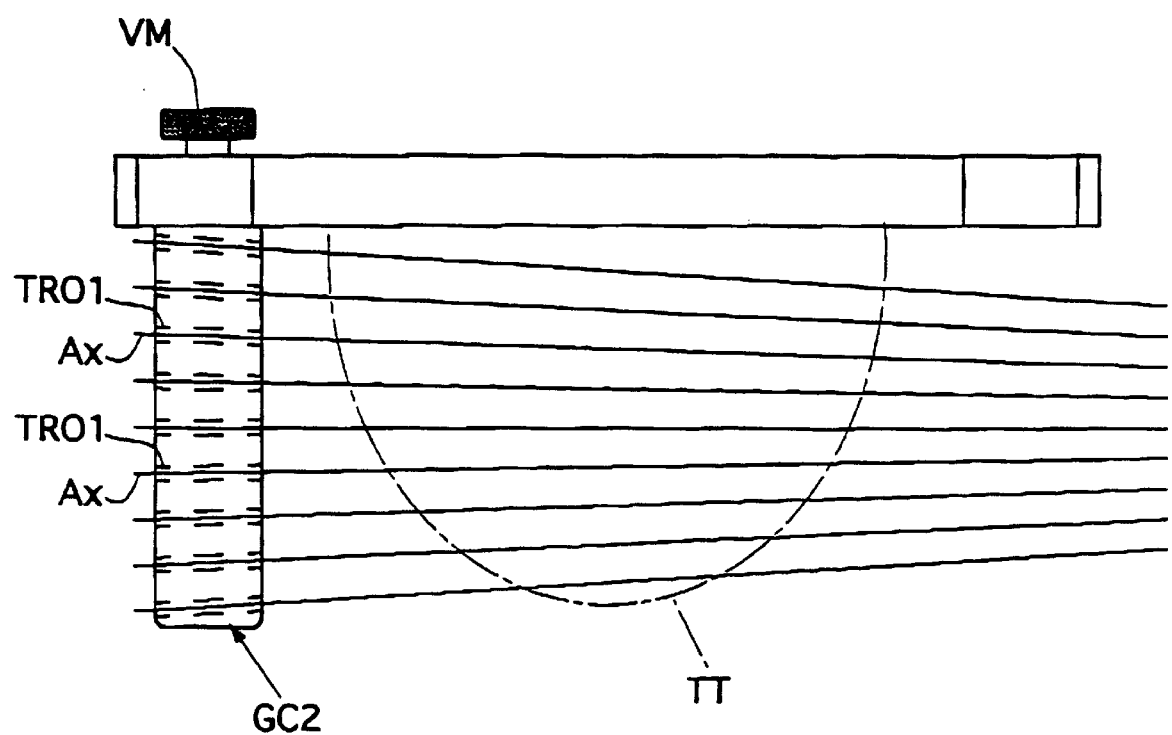
Figure 5:
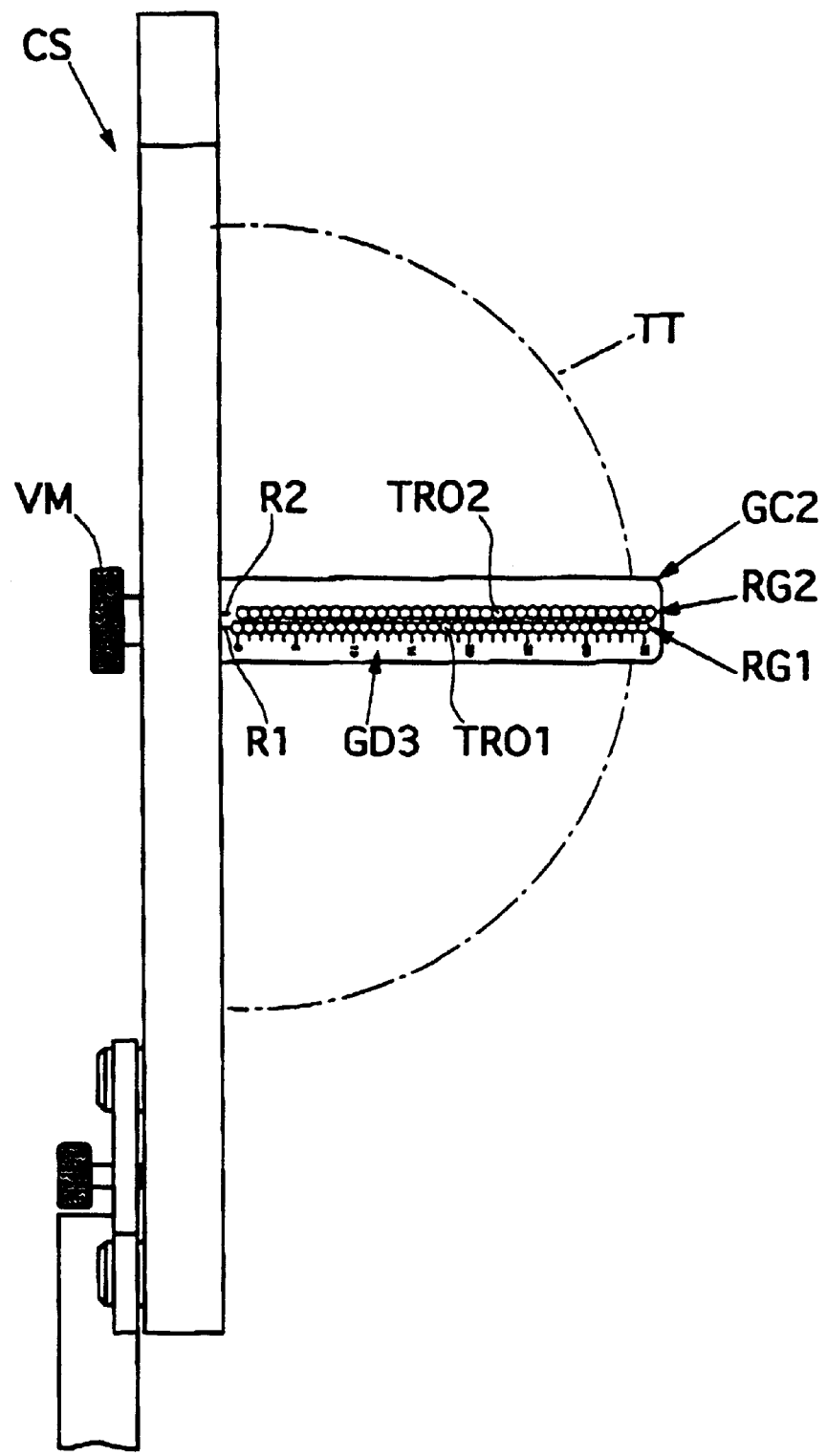

It is nevertheless particularly advantageous to use guide means such as the ones illustrated in FIGS. 3 to 5, instead of a thick guide grid.

It should be noted here that, for the sake of simplicity, the points Po for positioning the patient's cranium inside the chassis CS have been represented only in the front view, and have been omitted in the plan and left views.

On each of its vertical branches (this being for reasons of symmetry in order to allow the surgeon to work to the right or to the left of the patient's head TT), the chassis CS includes a curvilinear guide path Rg centered on the focus F of the X-ray beam. A guide element GC2 equipped with two columns of holes RG1 and RG2 slides along this guide path Rg. The first column RG1 corresponds exactly to the central column CL0 of the positioning grid Gr. All the holes TR01 in this first column are focused on the focus F of the tube Trx, that is to say their axes Ax converge towards the focus F. The second column of holes RG2 is identical to the first, apart from the fact that the holes TR02 in this second column are offset by a half hole spacing upwards, these holes TR02 still being focused on the focus of the tube Trx. Two marks R1 and R2 are etched at the top of each column of holes, these marks corresponding to the axes of each of the columns RG1 and RG2.

A graduation Gd is etched on the chassis CS and is used to locate exactly the position of the guide element GC2 along the guide path Rg. A knurled screw VM makes it possible to lock the guide element in an arbitrary position selected by the surgeon. With a view to this, the graduation Gd is formed by long lines and short lines. Putting the mark R1 next to the long lines allows the first column of holes RG1 to be positioned exactly, while putting the mark R2 next to the short lines of the graduation Gd allows the second column of holes RG2 to be positioned exactly.

Specifically, in the example described here, the long lines of the graduation Gd are numbered in correspondence with the columns CLj of the positioning grid.

The guide element is also provided with a graduation Gd3 corresponding to the rows of the positioning grid.

This embodiment facilitates access to the patient. These guide means are extremely simple to produce, and less expensive than the embodiment having a thick grid with about one hundred holes. This embodiment furthermore makes it possible to minimize human error in the selection of the piercing holes.

Thus, the use of guide means including holes whose axes converge towards the focal point of the source, makes it possible to use a conical X-ray beam of the type delivered in a conventional radiology room. The distance between the source and the image receiver is then of the order of 1 meter.

Although it is possible to use a thick perforated grid to form both the means for guiding the probes and the means for positioning them, it is particularly advantageous to use, for the second positioning means, a thin perforated grid whose holes have parallel axes and such that the conical projection of the guide holes of the guide means into the plane of the thin grid corresponds to the position of the holes in the positioning grid.

The use of a thin grid having holes with parallel axes makes it possible not only to use a conical X-ray beam, but also allows the grid to be seen more clearly on the radiographic images, without completely masking the anatomical structures.

While it would be possible, after having determined the position of the probes using the thin positioning grid, to withdraw this grid and replace it by a thick perforated grid forming the means for guiding the said probes, it is particularly advantageous if the first guide means include a guide element having at least a first column of guide holes whose respective axes all lie in the same first plane and are located by a first graduation corresponding to the location of the rows of the positioning grid. The axes of the guide holes in the element converge in the said first plane towards the object focal point of the source. This element is furthermore movable along a curvilinear guide path, centered on the object focal point, which is formed in the chassis and extends in a second plane perpendicular to the said first plane. The position of the element along the guide path is located by a second graduation corresponding to the location of the columns in the positioning grid. The curvature of the guide path is chosen while taking account of the distance separating the guide path from the object focal point and the aperture angle of the conical radiation so that the axes of the guide holes in the element converge towards the object focal point irrespective of the position of the element along the guide path.

It is furthermore particularly advantageous if the element includes a second column of guide holes which is parallel to the first, each hole in the second column being between two holes in the first column so as to correspond to a row interval of the positioning grid.

Various modifications in structure and/or function and/or steps may be made by one skilled in the art to the disclosed embodiments without departing from the scope and extent of the invention.

What is claimed is:

1. A radiology instrument comprising a source emitting X-radiation having a focal point, a radiological image receiver, a chassis arranged between the source of X-radiation and the image receiver in order to accommodate an object to be radiographed, and a positioning and guiding means which can be connected to the chassis and can intercept the X-radiation so as to position and guide probes intended to interact with the object wherein the radiation which is emitted by the source and intercepted by the positioning and guiding means is conical, and in that the positioning and guiding means comprises first guide means forming a retractable guide grid having holes whose respective axes converge towards the focal point of the source when the first guide means intercept the conical radiation, and a second positioning means forming a retractable positioning grid with holes, wherein the first guide means includes a perforated grid which also forms the second positioning means, the positions of the positioning holes relative to the chassis when the second positioning means are positioned so as to intercept the conical radiation corresponding to those of the guide holes relative to the chassis when the first guide means are positioned so as to accept the conical radiation, this positional correspondence accounting for the convent nature of the axes of the guide holes.

2. Instrument according to claim 1 wherein the second positioning means includes a grid and that the conical projection of the guide holes into the plane of the grid correspond to the position of the holes in the positioning grid.

3. Instrument according to claim 2 wherein the first guide means includes a perforated grid having a thickness greater than that of the gird of the second positioning means.

4. Instrument according to claim 2 wherein the first guide means include a guide element having at least a first column of guide holes whose respective axes all lie in the same first plane and are located by a first graduation corresponding to the location of the rows of the positioning grid, this element being movable along a curvilinear guide path which is formed in the chassis and extends in a second plane perpendicular to the said first plane, the position of the element along the guide path being located by a second graduation corresponding to the location of the columns of the positioning grid, in that the axes of the guide holes in the element converge in the said first plane towards the object focal point of the source, and in that the curvature of the guide path is chosen while taking account of the distance separating the guide path from the object focal point and the aperture angle of the conical radiation so that the axes of the guide holes in the element converge towards the object focal point irrespective of the position of the element along the guide path.

5. Instrument according to claim 4 wherein the element includes a second column of guide holes which is parallel to the first, each hole in the second column being between two holes in the first column so as to correspond to a row interval of the positioning grid.

* * * * *